United States Patent
Byrd et al.

(12)

(10) Patent No.: US 7,686,811 B2
(45) Date of Patent: Mar. 30, 2010

(54) SURGICAL COMPONENT FIXATION AND METHOD

(75) Inventors: Brian D. Byrd, North Webster, IN (US); Christopher M. Meek, Leesburg, IN (US); Adam H. Sanford, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 783 days.

(21) Appl. No.: 11/405,190

(22) Filed: Apr. 17, 2006

(65) Prior Publication Data

US 2007/0270871 A1 Nov. 22, 2007

(51) Int. Cl.
*A61B 17/58* (2006.01)
(52) U.S. Cl. ............ 606/88; 606/86 R; 606/87
(58) Field of Classification Search .......... 606/86 R–89
See application file for complete search history.

(56) References Cited

U.S. PATENT DOCUMENTS

| 3,727,611 | A | * | 4/1973 | Schultz ........................ 606/96 |
| 5,013,316 | A | * | 5/1991 | Goble et al. ................ 606/916 |
| 6,440,140 | B2 | * | 8/2002 | Bullivant et al. ............. 606/89 |
| 2004/0167519 | A1 | * | 8/2004 | Weiner et al. ................. 606/60 |

FOREIGN PATENT DOCUMENTS

WO WO 2004/021901 A1 * 3/2004

* cited by examiner

*Primary Examiner*—Eduardo C Robert
*Assistant Examiner*—Julianna N Harvey
(74) *Attorney, Agent, or Firm*—Baker & Daniels LLP

(57) ABSTRACT

An apparatus is provided for attaching a surgical component to a bone at a surgical site. The apparatus includes an elongated pin and a cam mounted to the pin. The cam is engaged with the surgical component such that rotating the cam about the shaft axis changes the surgical component position relative to the bone.

9 Claims, 3 Drawing Sheets

SURGICAL COMPONENT FIXATION AND METHOD

FIELD OF THE INVENTION

The present invention relates to an attachment mechanism and method for attaching surgical components to bones during orthopaedic surgical procedures. More particularly the present invention relates to an adjustable attachment mechanism.

BACKGROUND

Degenerative and/or traumatic damage to skeletal joints or other locations within a patient's body may require surgical intervention. During such surgical intervention, it is often necessary to position and/or support a surgical component at a desired location relative to the surgical site. For example, damage to the articular cartilage of a skeletal joint can result in pain and restricted motion. Prosthetic joint replacement is frequently utilized to alleviate the pain and restore joint function. In this procedure, the damaged parts of the joint are cut away and replaced with prosthetic components. Typically a resection guide is used to guide a cutter such as a saw blade or burr to cut a desired portion of the bone to prepare a seating surface for a prosthetic component. The resection guide must be carefully positioned to guide the cut at the appropriate location.

For example, during knee replacement surgery, an incision is made into the knee joint to expose the joint. Cutting guides defining cutting planes are positioned adjacent the articular surfaces of the tibia and femur. The cut guide locations are carefully adjusted to position the cut planes to guide the removal of portions of the articular surfaces of the tibia and femur. Prosthetic joint components are positioned on the cut bone surfaces to replace the resected portions of the tibia and femur in order to establish the desired alignment and mechanics of the joint. Proper orientation of the prosthetic joint components depends on the proper positioning of the cut guides.

SUMMARY

The present invention provides an apparatus for attaching a surgical component to a bone at a surgical site. The adjustable fixation mechanism includes an elongated pin and a cam mounted to the pin. The cam is engaged with the surgical component such that rotating the cam about the shaft axis changes the surgical component position relative to the bone.

In one aspect of the invention, the apparatus includes an elongated pin having a shaft with a first end, a second end, and a longitudinal shaft axis therebetween. The first end of the shaft is engageable with the bone. A cam is mounted to the second end of the shaft for rotation about the shaft axis. The cam has a cam surface defining at least two points spaced different radial distances from the shaft axis. The cam surface is engageable with the surgical component such that rotating the cam about the shaft axis changes the surgical component position relative to the bone.

In another aspect of the invention, a combination includes a surgical cut guide and a fixation pin for attaching the cut guide to a bone at a surgical site. The cut guide has a body defining a cut plane and is able to guide a cutter in the cut plane to cut the bone. The body further includes first and second fixation holes. The pin has a shaft with a first end, a second end, and a longitudinal shaft axis therebetween. The first end of the shaft is engageable with the bone. A cam is mounted to the second end of the shaft for rotation about the shaft axis. The cam has a cam surface defining at least two points spaced different radial distances from the shaft axis and the cam surface is engageable with the first fixation hole. The cam is rotatable about the shaft axis within the fixation hole to move the cut guide relative to the bone.

In another aspect of the invention, a method includes positioning a cut guide adjacent to a bone; inserting a first pin through the cut guide to engage the bone and attach the cut guide to the bone, the first pin having a first pin axis, a cam being mounted to the first pin for rotation about the first pin axis; and rotating the cam about the first pin axis to adjust the position of the cut guide relative to the bone.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 1:
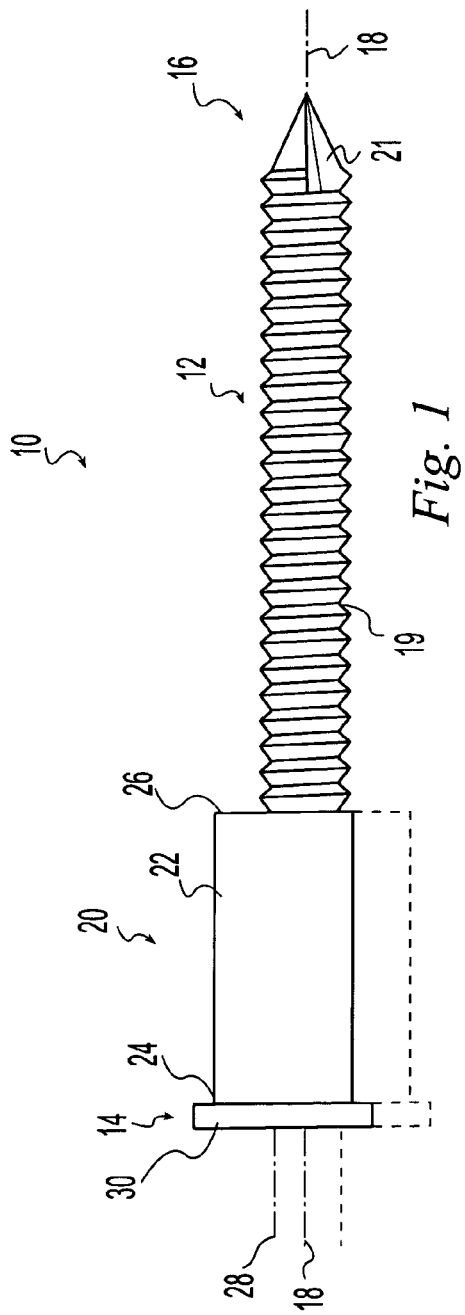
FIG. 1 is a side elevation view of an illustrative fixation pin according to the present invention.

Embodiments of the present invention include an elongated pin for attaching a surgical component adjacent to a bone at a surgical site. Surgical components may include implants, trial implants, drills, burrs, saws, lasers, thermal ablators, electrical ablators, retractors, clamps, cameras, microscopes, various guides, including cut guides, and/or other surgical components. Surgical sites may include a hip joint, knee joint, vertebral joint, shoulder joint, elbow joint, wrist joint, ankle joint, digital joint of the hand or foot, jaw, fracture site, tumor site, and/or other suitable surgical sites.

The pin includes a pin shaft having a central longitudinal shaft axis. The pin may have a smooth shaft for being driven by impacting the pin longitudinally into the bone. The pin may have a threaded shaft for being driven by screwing the pin longitudinally into the bone. The pin includes a cam projecting from the pin shaft and having points on the surface of the cam having different distances from the pin shaft axis. The pin may be positioned adjacent to a surgical component by driving the pin shaft into the bone and abutting the cam against a portion of the surgical component. Rotating the cam about the shaft axis changes the point on the cam abutting the portion of the surgical component and therefore allows the surgical component to change its spacing relative to the shaft axis. As points on the cam closer to the shaft axis abut the portion of the surgical component, the surgical component may move closer to the shaft axis. As points on the cam further from the shaft axis abut the portion of the surgical component, the surgical component must move further from the shaft axis. The surgical component may be trapped, biased, and/or otherwise compelled to follow the cam such that rotation of the pin about its axis forces the surgical component to move with the cam relative to the shaft axis. The pin may be used to adjust the position of a surgical component relative to any suitable parameter. For example, the cam may be rotated to vary medial/lateral angle and/or position, anterior/posterior angle and/or position, transverse angle and/or position, and/or any other suitable surgical component positioning parameter. For example, in a knee joint cut guide, the cam may be rotated to adjust the varus/valgus angle of the cut guide.

The cam may be circular, ovate, polygonal, linear, free form, and/or any other suitable shape. The cam may have a central axis parallel to the shaft axis. The cam axis may be collinear with the shaft axis or offset from the shaft axis. For example, a circular cam may have an axis offset from the shaft axis such that the shaft and cam are eccentric to one another and points on the cam circle are spaced different distances from the shaft axis. In another example, an ovate cam may have an axis concentric with the shaft axis. Due to the ovate shape of the cam, points on the surface of the cam are spaced different distances from the shaft axis. An ovate cam may also be eccentrically positioned.

The cam may engage a planar surface, curved surface, open surface, closed surface, and/or any suitable surface on the surgical component. For example, the surgical component may have a hole engageable with the cam such that rotation of the cam about the shaft axis causes the hole, and thus the surgical component to move with the cam. For example, a circular hole engaged with an eccentric circular cam will follow the eccentric cam as it rotates about the shaft axis. The pin may include a rotational engagement portion to facilitated rotation of the pin. The rotational engagement portion may include a driver engagement, a knob, a roughened surface, and/or other suitable rotational engagement portion. A driver engagement may include a headed or headless arrangement having splines, flats, sockets, slots, holes, and/or other suitable engagements. For example, the end of the pin may define a polygonal socket for engaging a complementary shaped driver.

The pin may have a head extending radially from the cam to limit longitudinal movement of the surgical component relative to the pin. For example, a surgical component may define a cam engaging hole and the cam may have a radially extending rim that prevents the surgical component from translating longitudinally off of the pin. Alternatively, the cam may be head-less to allow the removal and repositioning of the surgical component on the pin.

The cam may be a separate component from the pin and may be mounted to the pin for rotation about the pin. As the cam rotates about the pin, the surgical component follows the cam surface. For example, the cam may define a cylindrical cam body having a body center axis and a cam surface at the surface of the cylindrical cam body. The cam body may further define a pin engaging opening eccentric to the body axis. The opening engages the pin for rotation about the pin. As the cam rotates about the pin, the surgical component will follow the cam. The cam body may define a rotational engagement portion to facilitate rotating the cam.

The drawings illustrate a fixation mechanism for attaching a tibial cut guide to a tibia for angular adjustment of the cut guide relative to the tibia in knee replacement surgery. However, the illustrative fixation mechanism is by way of example only and it is contemplated that fixation mechanisms according to the present invention may be used to attach tibial cut guides, femoral cut guides, and any other surgical component at any other surgical site throughout the body.

FIGS. 1-4 show an illustrative adjustable fixation pin 10 including an elongated shaft 12 having proximal end 14, a distal end 16, and a longitudinal shaft axis 18 extending therebetween. The distal end 16 of the shaft 12 includes optional threads 19 for screw engagement with a bone. The threads 19 include a self tapping flute 21 at the distal end 16 to simplify insertion of the shaft 12 into the bone. The proximal end 14 defines a cylindrical cam 20 having a cam surface 22, a proximal end 24, a distal end 26, and a cam axis 28 extending along the center line of the cylindrical cam 20 from its proximal end 24 to its distal end 26. The cam axis 28 is offset from the shaft axis 18 such that the cam 20 is eccentrically positioned relative to the shaft 12. The cam further defines an optional head 30 in the form of a radially extending rim at the proximal end 24 of the cam. The pin 10 defines a hexagonal driver engaging socket 32 concentric to the shaft axis 18 to facilitate rotating the cam 20 about the shaft axis 18.

Figure 2:
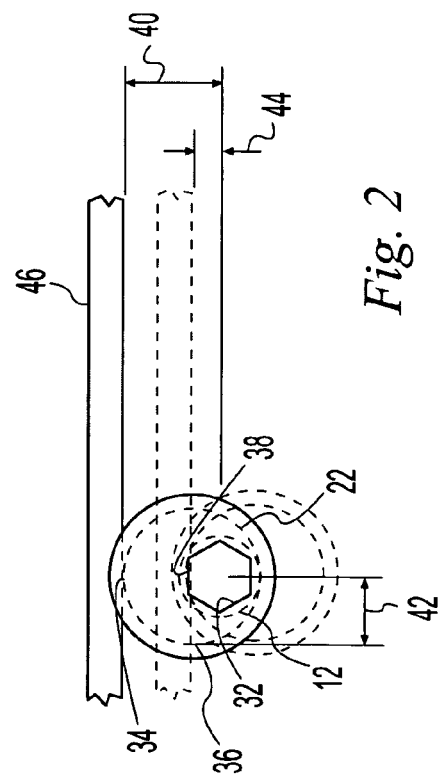
FIG. 2 is a front elevation view of the fixation pin of FIG. 1.

The cam surface 22 defines points 34, 36, 38 having different distances 40, 42, 44 (FIG. 2) from the shaft axis 18. An arbitrary surgical component 46 is shown resting on the cam surface 22 at a first point 34. The surgical component 46 is spaced a radial distance 40 from the shaft axis. When the cam 20 is rotated 1800 to position a second point 38 on the cam surface 22 in contact with the surgical component 46 the surgical component 46 is spaced a second, different distance 44 from the shaft axis 18. By rotating the cam 20 adjacent to the surgical component 46, the position of the surgical component relative to the pin 10 may be adjusted. In the example of FIG. 2, the surgical component 46 moves downwardly as the cam 20 is rotated between the two positions.

Figure 3:
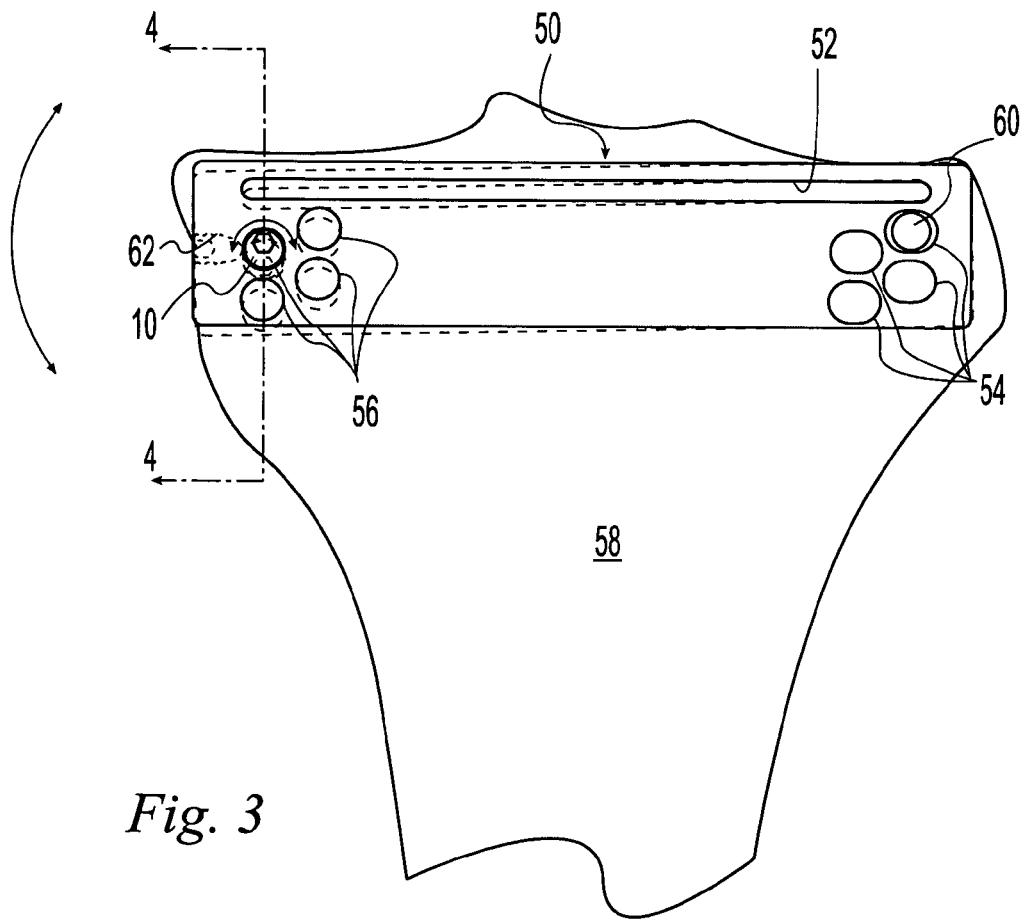
FIG. 3 is a front elevation view of a cut guide in use with the fixation pin of FIG. 1 mounted on a bone.
Figure 4:
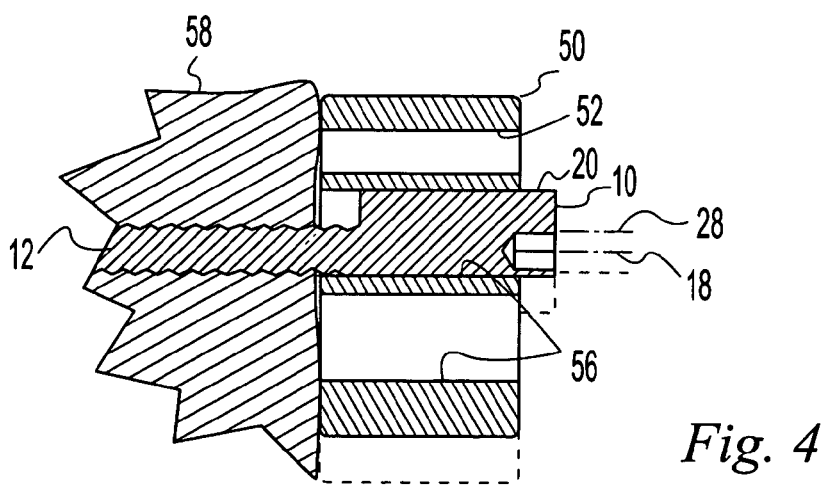
FIG. 4 is a side sectional view taken along line 4-4 of FIG. 3.

FIGS. 3 and 4 show a cut guide 50 having a cut slot 52 defining a cut plane. The cut guide 50 includes fixation holes 54, 56 for receiving fixation pins to attach the cut guide 50 to a bone 58 to guide a cutter (not shown) to cut the bone 58. The cut guide 50 is initially positioned on the bone 58 and pinned in place. In the illustrative example, a conventional straight pin 60 is inserted through a fixation hole 54 at the right side of the cut guide 50 and the adjustable fixation pin 10 is inserted through a fixation hole 56 at the left side of the guide 50. The conventional pin 60 forms a pivot point for rotational adjustment of the cut guide 50. As the adjustable fixation pin 10 is rotated in the hole 56 about the shaft axis 18, the cam surface 22 moves relative to the shaft axis 18 and the hole 56 follows the cam surface 22 to move the end of the cut guide 50. Thus, rotation of the adjustable fixation pin 10 adjusts the cut guide 50 angle relative to the conventional pin 60. The adjustable pin 10 maintains its rotational position due to frictional engagement with the bone 58. A threaded pin 10, as shown, will have a higher frictional engagement than an optional smooth shafted pin 10. If additional restraint on pin 10 rotation is desired, a set screw 62 may be threaded into the cut guide 50 to engage the pin 10. Furthermore, additional fixation pins may be inserted in additional fixation holes 54, 56 to lock the cut guide 50 angle. FIG. 3 illustrates an adjustable pin 10 and a conventional pin 60. However, an adjustable pin 10 could be used in both fixation holes 54, 56. Furthermore, the use of two adjustable pins 10 doubles the adjustment range as one end of the cut guide 50 can be moved down while the other end is moved up.

As the cam surface 22 of the adjustable pin 10 rotates toward or away from the conventional pin 60, the end of the cut guide with the adjustable pin 10 will pressed toward or away from the conventional pin 60 along a line between the two pins 10, 60. This side-to-side motion may be accommodated by flex and/or looseness in the pins and/or pin-to-bone interface. However, the side-to-side motion may also be accommodated by elongating one or more of the holes 54, 56.

The holes 54 on the right side of FIG. 3 have been elongated to accommodate side-to-side motion. Alternatively, the holes 56 on the left side of FIG. 3 may be elongated or both sets of holes 54, 56 may be elongated. Alternatively, the holes may remain circular and be enlarged to provide a loose fit between the pins and holes. However, enlarged holes will also allow vertical up-and-down motion of the guide relative to the pins and depending on the application may reduce the precision of the adjustment.

Figure 5:
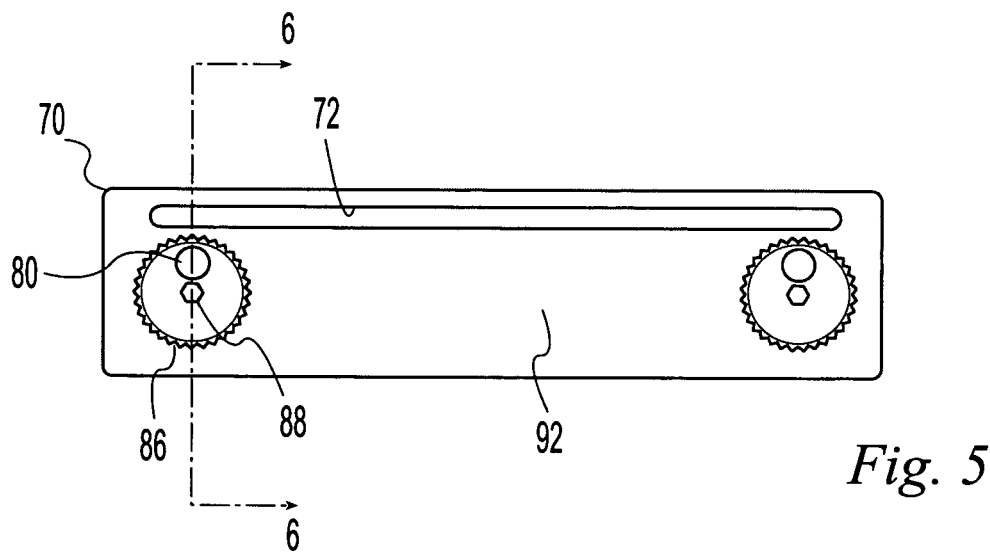
FIG. 5 is a front elevation view of a fixation pin and modular cam according to the present invention in use with a cut guide.
Figure 6:
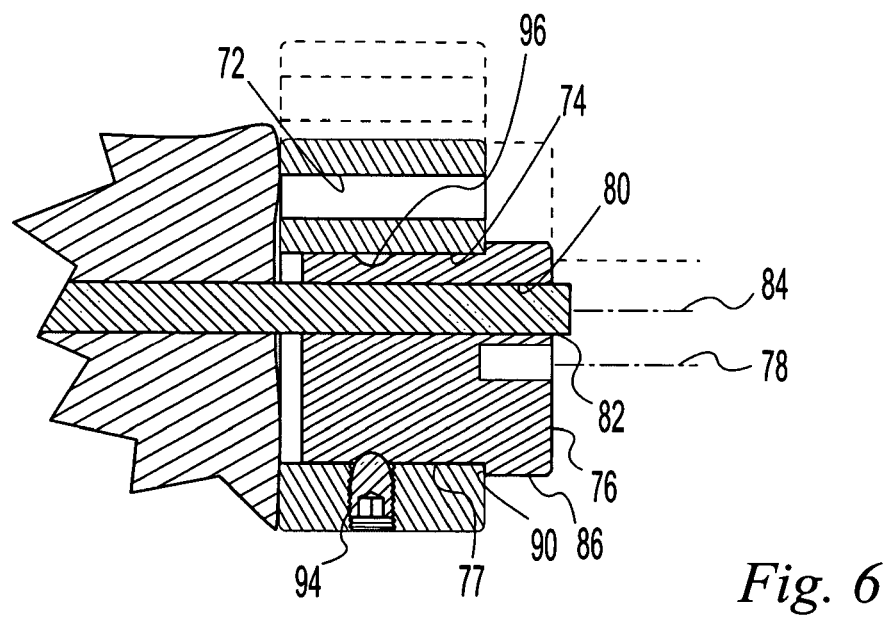
FIG. 6 is a side sectional view taken along line 6-6 of FIG. 5 showing the fixation pin, modular cam, and cut guide of FIG. 5 mounted on a bone.

FIGS. 5 and 6 show a cut guide 70 having a cut slot 72 defining a cut plane. The cut guide includes a fixation hole 74 extending through the cut guide 70. A cylindrical cam 76 having a cam surface 77 and a cam axis 78 is mounted in the fixation hole 74 for rotation within the hole about the cam axis 78. The cam 76 includes an eccentric hole 80 offset from the cam axis for engaging a pin 82 having a pin axis 84 for rotation of the cam 76 about the pin axis 84. As the cam 76 is rotated about the pin axis 84, the cam surface moves relative to the pin axis 84 and the hole 74 follows the cam surface 78 to move the end of the cut guide 70. In the illustrative example, a cam 76 is mounted at each end of the cut guide 70 so both ends can be adjusted.

The cam 76 includes a knob, or head, 86 to facilitate gripping and turning the cam 76.

The cam 76 further includes a driver engaging socket 88 to facilitate turning the cam 76 with a separate driver. The knob 86 extends radially outwardly from the cam 76 to define a shoulder 90 that abuts the front 92 of the cut guide 70 to help position the cam 76 longitudinally within the hole 74. A set screw 94 threads into the cut guide 70 and engages an annular groove 96 formed in the cam 76 to lock the cam longitudinally in the hole 74 and further to allow rotational tensioning and locking of the cam 76 in the hole 74.

In use, a surgical component is positioned on a bone and pinned in place with a pair of fixation pins. At least one of the fixation pins includes a cam that is rotatable to allow fine tuning of the surgical component position. A set screw may be used to tension and/or lock the cam position. Alternatively, the surgical component may be initially pinned with a pair of conventional pins. If it is necessary to later fine tune the surgical component position, a pin with a cam may be used. The user can choose to leave a conventional pin at the desired pivot point and replace the other pin with a pin and cam; either a unitary design like that of FIGS. 1-4 or separate components like that of FIGS. 5-6.

Although examples of an adjustable fixation pin and cam arrangement and its use have been described and illustrated in detail, it is to be understood that the same is intended by way of illustration and example only and is not to be taken by way of limitation. The invention has been illustrated with cylindrical cams used to adjust the angular position of a cut guide used in knee replacement surgery. However, the adjustable fixation pin and cam arrangement may be configured with differently shaped cams and to adjustably support other surgical components adjacent to other surgical sites. Accordingly, variations in and modifications to the adjustable fixation pin and cam arrangement and its use will be apparent to those of ordinary skill in the art, and the following claims are intended to cover all such modifications and equivalents.

What is claimed is:

1. A combination of a surgical cut guide and a fixation pin for attaching the cut guide to a bone at a surgical site, the combination comprising:
   a cut guide having a body defining a cut plane and able to guide a cutter in the cut plane to cut the bone, the body further defining first and second fixation holes;
   an elongated first pin having a shaft with a first end, a second end, and a longitudinal shaft axis therebetween, the first end of the shaft being engageable with the bone;
   a cam mounted to the second end of the shaft for rotation about the shaft axis, the cam having a cam surface defining at least two points spaced different radial distances from the shaft axis, the cam surface being engageable with the first fixation hole; and
   a second pin engageable with the second fixation hole and the bone, the first and second pins operable to secure the cut guide to the bone in a first position in which the cut plane forms a first angle with an anatomic axis of the bone, and a second position in which the cut plane forms a second angle different from the first angle to the anatomic axis of the bone, whereby rotation of the cam about the shaft axis of the first pin effects rotation of the cut guide about the second pin to effect movement of the cut guide between the first and second positions.

2. The combination of claim 1 wherein the shaft comprises threads to threadably engage the bone.

3. The combination of claim 1 wherein the cam comprises a cylindrical body defining a central longitudinal cam axis, the cam axis being radially offset from the shaft axis.

4. The combination of claim 1 wherein the pin further comprises means for receiving a driver in torque transmitting relationship.

5. The combination of claim 1 wherein the cam comprises a head extending radially outwardly to limit longitudinal movement of the cut guide relative to the cam.

6. The combination of claim 1 wherein the cam is an integral part of the shaft and the cam and shaft rotate together about the cam axis.

7. The combination of claim 1 wherein the cam is a separate component from the pin mounted for rotation relative to the pin.

8. The combination of claim 7 wherein the cam comprises a cylindrical body defining a central cam axis, the cam having a mounting hole eccentrically offset from the cam axis, the cam being mounted to the shaft with the mounting hole engaging the shaft for eccentric rotation of the cam about the shaft.

9. The combination of claim 1 further comprising a set screw threadably engaging the cut guide and communicating with the first fixation hole, the set screw being operable to restrain rotation of the cam.

* * * * *